(12) United States Patent
Ebel

(10) Patent No.: US 6,515,154 B2
(45) Date of Patent: Feb. 4, 2003

(54) ACETOACETIC ACID DERIVATIVES, PROCESS FOR THEIR PREPARATION AND THEIR USE

(75) Inventor: Klaus Ebel, Lampertheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 60 days.

(21) Appl. No.: 09/847,300

(22) Filed: May 3, 2001

(65) Prior Publication Data

US 2001/0056195 A1 Dec. 27, 2001

(30) Foreign Application Priority Data

May 17, 2000 (DE) .......................................... 100 23 886

(51) Int. Cl.$^7$ ................................................. C11C 3/00
(52) U.S. Cl. ........................ 554/164; 554/162; 554/163; 568/412
(58) Field of Search .................................. 664/162, 163, 664/164; 568/412

(56) References Cited

U.S. PATENT DOCUMENTS

| 5,120,880 A | * | 6/1992 | Huellmann et al. | ......... 568/412 |
| 5,247,122 A | | 9/1993 | Witzemann et al. | ......... 560/51 |

FOREIGN PATENT DOCUMENTS

| EP | 400 509 | 12/1990 |
| WO | WO 00/01648 | 1/2000 |

OTHER PUBLICATIONS

Allen et al. "Synthetic Aspects of Free–Radical Addition. Part I. Radical–alkylation of Malonic Ester and Related Compounds" J. Chem Soc. vol. 11 (1962) pp. 4468–4475.
Sakurai et al. "Chemistry of Organosilicon Compounds" J. Organometallic Chemistry Bol. 264 (1984) pp. 229–237.
Fujisawa et al. "One–step Synthesis of Long–chain Aliphatic α, ω–Dicarboxylic Acids Utilizing the Copper–catalyzed Reaction of β–Priopiolactone with α,ω–Di–Grignard Reagents" Bull. Chem. Soc. of Japan vol. 56 (1983) pp. 345–346.
Matsumoto et al. "Conversion of Disilanes of Functional Monosilanes IV.[1]) Synthesis of Methyldchlorosilane and Dlmethylchlorosilane by the Reaction of Methylchlorodisilanes with Hydrogen Chloride in the Presence of Tetrakis (tripehnylphosphine) palladium (0)" Bull. Chem. Soc. of Japan vol. 56 (1978) pp. 1913–1914.
Tsuji et al. "Synthesis of 1,15–Hexadecanedione, A Precursor of Muscone, from Butadiene" Chemistry Letters (1976) pp. 773–774.
Wynberg et al. "The Chemistry of Polythienyls" J. Am. Chem. Soc. vol. 82 (1960) pp. 1447–1450.
Stoll et al. "Synthèses de Produits marcrocycliques à odeur musquée" Helvetica Chimica Acta. vol. 30 (1947) pp. 2019–2023.
Schulte–Ette "Macrocyclic Ring Closure of OH–assisted *Prins* Reaction. A New and Efficient Synthesis of (*R,S*)–Muscone" Helvetica Chimica Acta vol. 62 (1979) pp. 26732681.
Bienz et al. "Eine neue Synthese von Muscon und *Exalton*®. Die Enamin–Route der Tingerweiterungsreaktion" Helvetica Chimica Acta vol. 71 (1988) pp. 1704–1708.
Ziegler "Methoden zur Herstellung und Umwandlung großer Ringsysteme[1]" Helvetica Chimica Acta vol. 71 (1988) pp. 729–815.

* cited by examiner

*Primary Examiner*—Deborah D. Carr
(74) *Attorney, Agent, or Firm*—Keil & Weinkauf

(57) ABSTRACT

The present invention relates to acetoacetic acid derivatives of the formula Ia or Ib, to processes for their preparation and to their use for the preparation of 2,15-hexadecanedione. The invention further relates to the use of the compounds of the formula Ia or Ib

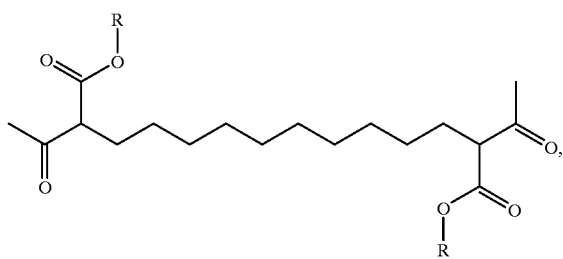

(Ia)

(Ib)

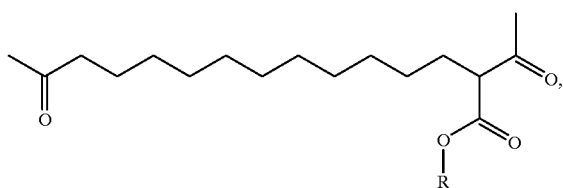

where R is an optionally substituted straight-chain or branched $C_1$–$C_6$-alkyl, $C_1$–$C_6$-alkoxyalkyl or phenyl radical, alkoxy groups are a combination of an alkyl group according to the above definition with an oxygen atom, e.g. methoxy, ethoxy, propoxy, butoxy or pentoxy groups, which comprises adding an acetoacetic ester of the formula II

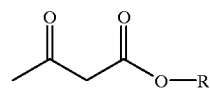

to 1,9-decadiene by a free-radical means, as intermediate for the preparation of muscone (3-methylcyclopentadecanone).

7 Claims, No Drawings

ACETOACETIC ACID DERIVATIVES, PROCESS FOR THEIR PREPARATION AND THEIR USE

Acetoacetic acid derivatives, process for their preparation and their use

The present invention relates to acetoacetic acid derivatives of the formula Ia or Ib, to processes for their preparation and to their use for the preparation of 2,15-hexadecanedione. The invention further relates to the use of the compounds of the formula Ia or Ib as intermediate for the preparation of muscone (3-methylcyclopentadecanone).

Muscone(3-methylcyclopentadecanone) of the formula III

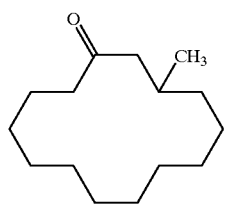

(III)

is one of the most important ingredients of the natural musk extracts which are very highly sought after in perfumery. Because of the extremely high cost of natural extracts, the synthetic preparation of III is of great interest, particularly since III is far superior to all other known musk fragrances, such as tetralin or nitro musk compounds.

The preparation methods used hitherto are based mainly on ring enlargement reactions, starting from cyclododecanone (cf. for example Helv. Chim. Acta 71 (1988), pp. 1704–1718, and literature cited in loc. Cit.). All of these methods have a multistage process step, which is sometimes extremely involved, and they are therefore unattractive for commercial exploitation.

All known synthesis methods involve intramolecular condensation reactions, such as aldol, Dieckmann or acyloin condensation (see here Houben-Weyl, Methoden der organischen Chemie [Methods of organic chemistry], Vol. 4/2, pp. 729–815). All of these methods have the major disadvantage that relatively good yields of macrocycles are only obtained in very high dilution.

Helv. Chim. Acta, 62 (1979), pages 2673–2680, presents a new type of synthesis process for muscone based on 4,8-dodecadienediol. The key step here is the acid-catalyzed intramolecular cyclization of an open-chain hydroxyacetal to give bicyclic dihydropyran, where, however, because of the required dilution principle, large amounts of solvent are required, as a result of which this process can only be sensibly used for the synthesis of laboratory amounts.

One possibility, which is in itself very good, for preparing II seems to the aldol condensation starting from hexadecane-2,15-dione first described by Stoll (cf. Helv. Chim. Acta, 30 (1974), pages 2019–2023).

However, this process was burdened with considerable disadvantages:

1) The preparation possibilities for the 2,15-diketone required as starting material were hitherto unsatisfactory.
2) The yields achievable in the aldol condensation are relatively low despite working in heavily diluted solutions (according to loc. cit. 17%).

A particular disadvantage of this synthesis is the use of the costly and also toxicologically unacceptable 1,10-dibromodecane.

In addition, the synthesis below starting from 2,2',5',2"-terthienyl was presented in J. Am. Chem. Soc. 82 (1960), pages 1447–1450.

However, this synthesis is unsuitable for the synthesis of relatively large amounts of diketone due to the poor accessibility of the starting material.

Two further processes for the preparation of the diketone, each starting from butadiene, have been described by Tsuji et al.:

a) in Chem. Lett. 1976, pages 773–774 and
b) in Bull. Chem. Soc. Japan, 51 (1978), page 1915.

Both processes use expensive palladium catalysts, as a result of which these syntheses too become unattractive for industrial use.

Furthermore, Bull. Chem. Soc. Japan, 56 (1983), pages 345–346, discloses a process for the preparation of IIa starting from α,ω-tetradecanedicarboxylic acid. A disadvantage of this process is the poor accessibility of the starting compound.

Moreover, J. Organomet. Chem. 264 (1984), pages 229–237, discloses a process for the preparation of IIa starting from $(CH_3)_3Si—CH_2—CH=CH—CH_2—CH_2—C(CH_3)=CH—CH_2—Si(CH_3)_3$. In addition to the poor accessibility of the starting compound, a disadvantage of this process is the need to use problematical reagents, such as readily flammable potassium hydride.

Also known is the preparation, disclosed in EP-B 0400509 but very complex, of 2,15-hexadecanedione which, inter alia, includes steps such as an oxidation of a diol using sodium hypochlorite to give the dialdehyde and either a Wittig reaction or a Grignard reaction.

It is an object of the present invention to find a simple and economical method for the preparation of 2,15-hexadecanedione and thus also for the preparation of muscone, without the disadvantages specified in the prior art.

We have found that this object is achieved according to the invention by a process for the preparation of compounds of the formula Ia or Ib

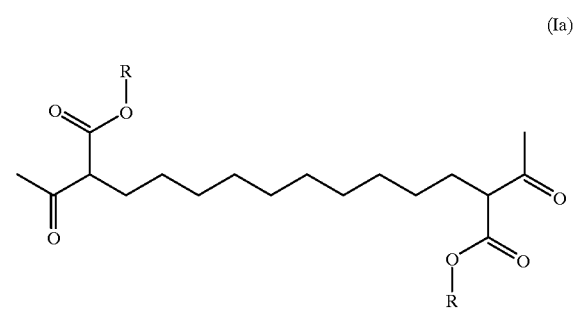

(Ia)

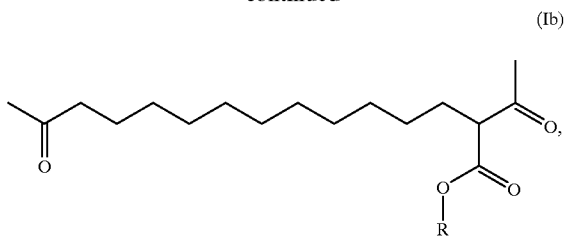

(Ib)

where R is an optionally substituted straight-chain or branched $C_1$–$C_6$-alkyl, $C_1$–$C_6$-alkoxyalkyl or phenyl radical, which comprises adding an acetoacetic ester of the formula II

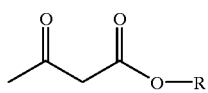

to 1,9-decadiene by a free-radical means, and hydrolyzing and carboxylating the compounds of the formula Ia or Ib thus synthesized (scheme 1)

Scheme 1

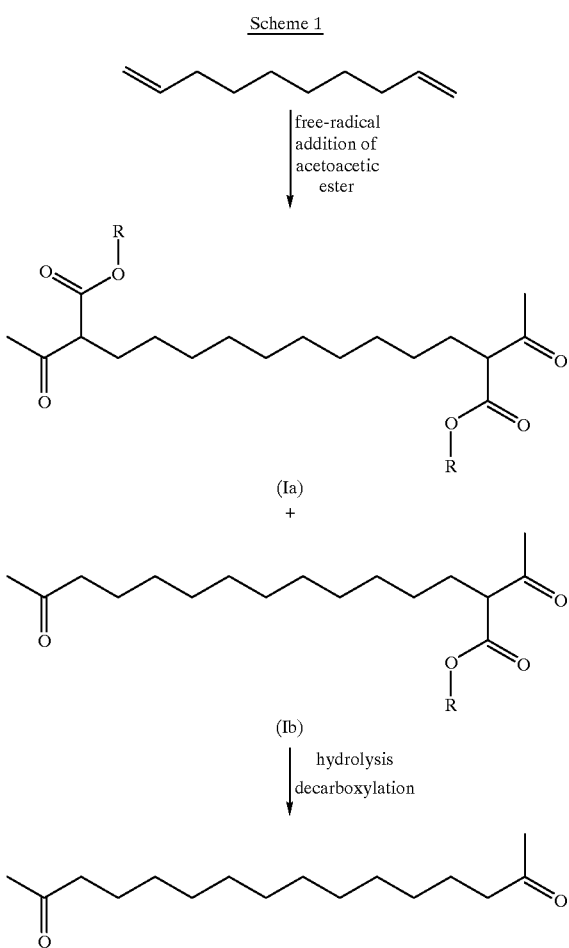

In the process, two molecules of an ester of acetoacetic acid are firstly added, in a free-radical reaction, to the 1,9-decadiene which can be prepared very easily and cost-effectively by metathesis of cyclooctene with ethylene.

The resulting addition products are the corresponding esters of 2,13-bisacetyl-1,14-tetradecanedioic acid (Ia). In addition, the corresponding ester of 2-acetyl-14-oxopentadecanoic acid (Ib) may also be formed as early as during the free-radical addition. This compound is formed by decarboxylation of an ester group of the primary product.

Said compounds can be decarboxylated in the manner customary for keto esters to give 2,15-hexadecanedione. From the beta-keto esters it is also possible to prepare the corresponding beta-keto acids or salts of the acids, which can both arise as intermediates during cleaving-off of the ester groups. However, the beta-keto acids are not stable compounds since they very readily decarboxylate upon heating to give 1,15-hexadecanedione. They are therefore preferably isolated in the form of their metal salts.

Alkyl in the case of the radical R means, unless stated otherwise, alone or in combination with alkoxy, a straight-chain, branched, saturated or unsaturated radical having 1 to 6 carbon atoms, such as, for example, the methyl, ethyl, propyl, isopropyl, tert-butyl, tert-pentyl, allyl or propynyl radicals.

Alkyl is preferably the methyl, ethyl, propyl, tert-butyl or tert-pentyl radicals.

Alkoxy groups mean a combination of an alkyl group according to the above definition with an oxygen atom, e.g. methoxy, ethoxy, propoxy, butoxy or pentoxy groups. Particular preference is given to the 2-methoxyethyl radical.

A simple two-stage process for the preparation of 2,15-hexadecanedione thus results, which signifies significant progress over the prior art.

Since the 2,15-diketones of the formula Ia or Ib can be prepared by the process described above in a technically simple manner, an industrially simple and advantageous synthesis route to the sought-after musk fragrance muscone is obtained.

One method of the subsequent intramolecular aldol condensation of the 2,15-hexadecanedione prepared according to the invention to give muscone is disclosed, for example, in EP-B 0400509.

The examples below serve to illustrate the invention in more detail without, however, limiting it thereto.

EXAMPLES

Example 1

Preparation of dimethyl 2,13-bisacetyl-1,14-tetradecanedioate and methyl 2-acetyl-14-oxopentadecanoate A mixture of 116 g (1 mol) of methyl acetoacetate, 36 g (0.25 mol) of 96% strength 1,9-decadiene and 14.6 g (0.1 mol) of di-tert-butyl peroxide is added, with stirring, at 160° C. to 174 g (1.5 mol) of methyl acetoacetate within 2 h. The mixture is then stirred for a further 1 h at 160° C. in order to completely decompose the peroxide. Finally, the excess methyl acetoacetate is distilled off under reduced pressure. The residue of 82 g comprises, according to GC analysis, 57% dimethyl 2,13-bisacetyl-1,14-tetradecanedioate (46.7 g=0.14 mol) and 4% methyl 2-acetyl-14-oxopentadecanoate (3.3 g=0.01 mol). This corresponds to a total yield of both products of 0.15 mol=60% yield.

The pure compounds can be isolated by column chromatography over silica gel (mobile phase: toluene/acetone 4:1).

¹H-NMR data (CDCl₃):

Dimethyl 2,13-bisacetyl-1,14-tetradecanedioate:

δ(ppm)=1.3 (s, 16H), 1.8 (m, 4H), 2.2 (s, 6H), 3.4 (t, 2H), 3.7 (s, 6H)

Methyl 2-acetyl-14-oxopentadecanoate:

δ(ppm)=1.3 (s, 18H), 1.8 (m, 2H), 2.2 (s, 6H), 2.5 (t, 2H), 3.4 (t, 1H), 3.7 (s, 3H)

Example 2

Preparation of 2,15-hexadecanedione from the product from example 1

0.37 g (1 mmol) of dimethyl 2,13-bisacetyl-1,14-tetradecanedioate were dissolved in 20 ml of DMSO and refluxed with 0.06 g (0.1 mmol) of sodium chloride and 0.04 g (2 mmol) of water for 3 h at 155 to 160° C. For work-up, the DMSO is firstly distilled off under reduced pressure, and the residue is distilled using a bulb tube. This gives 0.21 g of hexadecane-1,15-dione. Accordingly, the yield of 1,15-hexadecanedione is 82%, based on 1,9-decadiene.

Example 3

Preparation of diethyl 2,13-bisacetyl-1,14-tetradecanedioate and ethyl 2-acetyl-14-oxopentadecanoate 36 g (0.25 mol) of 95% strength 1,9-decadiene and 14.6 g (0.1 mol) of di-tert-butyl peroxide are added dropwise from separate dropping funnels to 325 g (2.5 mol) of ethyl acetoacetate with stirring at 160° C. over the course of 2 h. During this, the temperature drops slowly to 150° C. and the solution starts to boil. The mixture is then refluxed for a further 1 h at 150° C. in order to completely decompose the peroxide. Finally, the excess ethyl acetoacetate is distilled off under reduced pressure. The residue of 196 g comprises, according to GC analysis, 27% diethyl 2,13-bisacetyl-1,14-tetradecanedioate (53 g=0.14 mol) and 2% ethyl 2-acetyl-14-oxopentadecanoate (3.9 g=0.01 mol). This corresponds to an overall yield of both products of 0.15 mol=60% yield.

The pure compounds can be isolated by column chromatography over silica gel (mobile phase: n-hexane/acetone 4:1).

¹H-NMR data (CDCl₃):

Diethyl 2,13-bisacetyl-1,14-tetradecanedioate:

δ(ppm)=1.3 (m (t), 22H), 1.8, (m, 4H), 2.2 (s, 6H), 3.4 (t, 2H), 4.2 (q, 4H)

Ethyl 2-acetyl-14-oxopentadecanoate:

δ(ppm)=1.3 (m (t), 21H), 1.8 (m, 2H), 2.2 (s, 6H), 2.5 (t, 2H), 3.4 (t, 1H), 4.2 (q, 2H)

Example 5

2,13-Bisacetyl-1,14-tetradecanedioic acid and its sodium salt

A solution of 0.37 g (1 mmol) of dimethyl 2,13-bisacetyl-1,14-tetradecanedioate and 0.18 g (2.2 mmol) of 50% strength sodium hydroxide solution in 50 ml of methanol is refluxed for 18 h. The methanol is then distilled off under reduced pressure. The residue (0.45 g) comprises the desired sodium salt.

The free acid is obtained by careful neutralization of the sodium salt with hydrochloric acid. It decarboxylates very readily via 2-acetyl-14-oxopentadecanoic acid as intermediate to give 1,15-hexadecanedione and was not isolated in pure form.

Example 6

Preparation of hexadecane-1,15-dione without isolation of the intermediates 57.6 g (0.4 mol) of 96% strength 1,9-decadiene and 23.4 g (0.16 mol) of di-tert-butyl peroxide are added dropwise from separate dropping funnels (immersed), at 160° C., to 464 g (4 mol) of methyl acetoacetate over the course of 2 h, and the mixture is then refluxed for a further 1 h. The excess acetoacetate is then distilled off under reduced pressure. This gives 148 g of an oily residue which is further reacted directly. This residue is dissolved in 400 ml of DMSO and refluxed with 35.6 g (0.44 mol) of sodium chloride and 14.4 g (0.08 mol) of water for 3 h at 155 to 160° C. According to GC analysis, the mixture comprises 10.7 area % hexane-1,15-dione and also 1.5 area % methyl 2-acetyl-14-oxopentadecanoate. For work-up, the DMSO is firstly distilled off under reduced pressure, and the residue (137 g) is distributed between 700 ml of ethyl acetate and 100 ml of water, and the ethyl acetate phase is washed again with 100 ml of water. The ethyl acetate phase is dried and concentrated under reduced pressure. This gives 102 g of residue with a content, according to GC, of 37% by weight of hexadecane-1,15-dione. Accordingly, the yield of 1,15-hexadecanedione is 42%, based on 1,9-decadiene.

The residue is distilled under a high vacuum, 48 g of 74% strength 1,15-hexadecanedione passing over, which corresponds to a yield of 36%.

I claim:

1. A process for the preparation of esters of the formula Ia and Ib

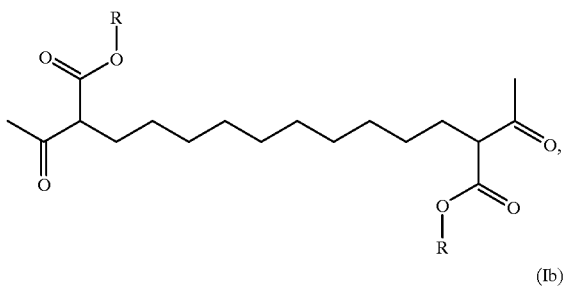

(Ia)

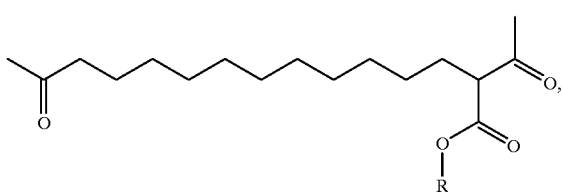

(Ib)

where R is an optionally substituted straight-chain or branched C₁–C₆-alkyl, C₁–C₆-alkoxyalkyl or phenyl radical, which comprises adding an acetoacetic ester of the formula II

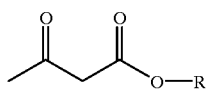

to 1,9-decadiene by a free-radical means.

2. A process for the preparation of a mixture of the esters of the formulae Ia and Ib as claimed in claim 1.

3. A compound of the formula Ia or Ib

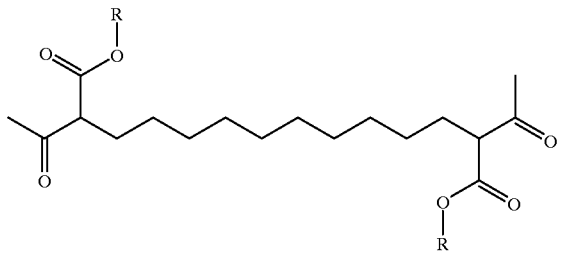

(Ia)

(Ib)

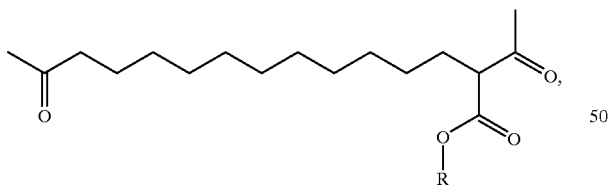

where R=an optionally substituted straight-chain or branched $C_1$–$C_6$-alkyl, $C_1$–$C_6$-alkoxyalkyl or phenyl radical, alkoxy groups are a combination of an alkyl group according to the above definition with an oxygen atom, e.g. methoxy, ethoxy, propoxy, butoxy or pentoxy groups, ester thereof, optically active form, racemate, tautomer, diastereomer mixture and salt thereof.

4. A process for the preparation of 1,15-hexadecanedione, which comprises adding the esters of acetoacetic acid of the formula II to 1,9-hexadiene by free-radical means and then decarboxylating the compounds of the formula Ia or Ib to give 1,15-hexadecanedione.

5. A process for the preparation of muscone of the formula III

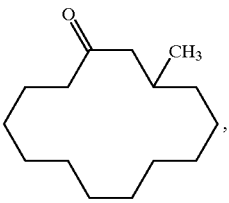

(III)

which comprises adding esters of acetoacetic acid (II) to 1,9-decandiene, decarboxylating the addition products Ia or Ib to give 1,15-hexadecanedione, then cyclizing the latter in the gaseous phase to give muscone in admixture with unsaturated muscone derivatives, and finally hydrogenating the unsaturated muscone derivatives to give muscone.

6. The preparation of 2,15-hexadecanedione by decarboxylating one of the following compounds

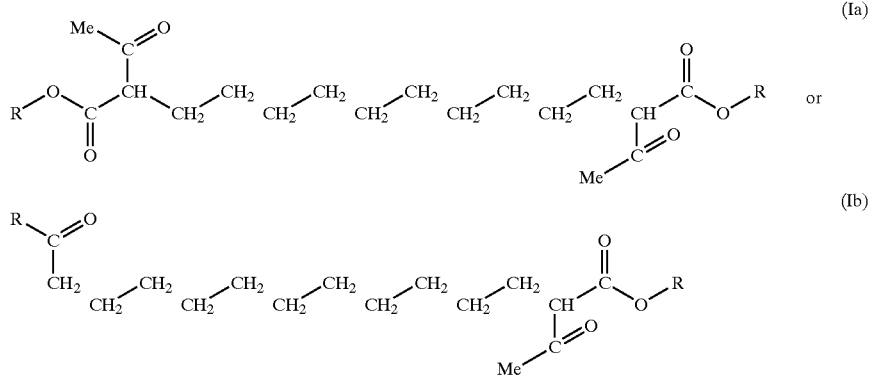

(Ia)

(Ib)

where R is an optionally substituted straight-chaim or branched C1–C6-alkyl, C1–C6- alkoxyalkyl or phenyl radical.

7. The preparation of muscone of the formula

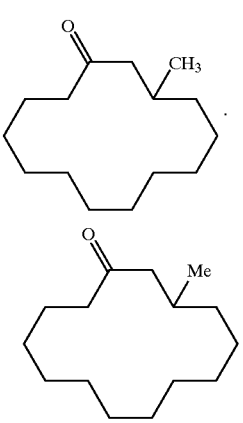

(III)

by decarboxylating one of the following compounds

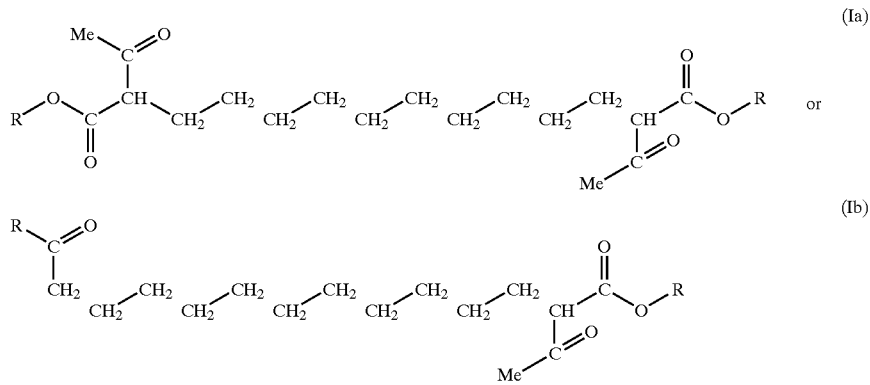
(Ia)
(Ib)
where R is an optionally substituted straight-chaim or branched C1–C6-alkyl, C1–C6- alkoxyalkyl or phenyl radical.
* * * * *

UNITED STATES PATENT AND TRADEMARK OFFICE
CERTIFICATE OF CORRECTION

PATENT NO. : 6,515,154 B2
DATED : February 4, 2003
INVENTOR(S) : Klaus Ebel

It is certified that error appears in the above-identified patent and that said Letters Patent is hereby corrected as shown below:

Column 8,
Line 43, "straight-chaim" should be -- straight-chain --.
Line 44, "C1-C6-alkyl, C1-C6-alkoxyalkyl" should be
-- $C_1$-$C_6$-alkyl, $C_1$-$C_6$-alkoxyalkyl --.
Lines 49-56, delete the first formula.

Column 9,
Line 1, after the formulae, "straight-chaim" should be -- straight-chain --.
Line 2, after the formulae, "C1-C6-alkyl, C1-C6-alkoxyalkyl" should be
-- $C_1$-$C_6$-alkyl, $C_1$-$C_6$-alkoxyalkyl --.

Signed and Sealed this

Twenty-seventh Day of May, 2003

JAMES E. ROGAN
*Director of the United States Patent and Trademark Office*